US010857236B2

(12) United States Patent
Dékány et al.

(10) Patent No.: US 10,857,236 B2
(45) Date of Patent: Dec. 8, 2020

(54) SUSTAINED RELEASE NANOCOMPOSITE, A PROCESS FOR PRODUCING THE SAME AND USE THEREOF

(71) Applicant: SZEGEDI TUDOMÁNYEGYETEM, Szeged (HU)

(72) Inventors: Imre Dékány, Szeged (HU); István Krizbai, Szeged (HU); Zsófia Majláth, Szeged (HU); József Toldi, Szeged (HU); Noémi Varga, Bugac (HU); László Vécsei, Szeged (HU)

(73) Assignee: Szegedi Tudományegyetem, Szeged (HU)

( * ) Notice: Subject to any disclaimer, the term of this patent is extended or adjusted under 35 U.S.C. 154(b) by 0 days.

(21) Appl. No.: 15/747,860

(22) PCT Filed: Jul. 28, 2016

(86) PCT No.: PCT/HU2016/050034
§ 371 (c)(1),
(2) Date: Jan. 26, 2018

(87) PCT Pub. No.: WO2017/021748
PCT Pub. Date: Feb. 9, 2017

(65) Prior Publication Data
US 2018/0221502 A1 Aug. 9, 2018

(30) Foreign Application Priority Data
Jul. 31, 2015 (HU) .................................. 1500356

(51) Int. Cl.
| | |
|---|---|
| *A61K 47/64* | (2017.01) |
| *A61K 9/51* | (2006.01) |
| *A61K 31/355* | (2006.01) |
| *A61K 31/198* | (2006.01) |
| *A61K 47/58* | (2017.01) |
| *A61K 47/69* | (2017.01) |
| *A61K 9/00* | (2006.01) |
| *A61K 31/137* | (2006.01) |
| *A61K 31/192* | (2006.01) |
| *A61K 31/47* | (2006.01) |

(52) U.S. Cl.
CPC .......... *A61K 47/643* (2017.08); *A61K 9/0085* (2013.01); *A61K 9/5146* (2013.01); *A61K 9/5161* (2013.01); *A61K 9/5169* (2013.01); *A61K 31/137* (2013.01); *A61K 31/192* (2013.01); *A61K 31/198* (2013.01); *A61K 31/355* (2013.01); *A61K 31/47* (2013.01); *A61K 47/58* (2017.08); *A61K 47/6931* (2017.08)

(58) Field of Classification Search
CPC .. A61K 47/643; A61K 9/5161; A61K 9/5169; A61K 9/5146; A61K 31/355; A61K 31/198; A61K 47/58; A61K 47/6931; A61K 9/0085; A61K 31/137; A61K 31/192; A61K 31/47; A61K 47/30; A61K 47/42
See application file for complete search history.

(56) References Cited

U.S. PATENT DOCUMENTS

| | | | | |
|---|---|---|---|---|
| 2003/0069757 | A1* | 4/2003 | Greenberg | ............. G16H 10/20 705/2 |
| 2005/0281884 | A1* | 12/2005 | Adair | ................. A61K 49/0041 424/489 |
| 2011/0038939 | A1 | 2/2011 | Lvov et al. | |
| 2013/0017148 | A1 | 1/2013 | Larsen et al. | |

FOREIGN PATENT DOCUMENTS

WO 2008/107729 A1 9/2008

OTHER PUBLICATIONS

Xie et al., Chinese Journal of Polymer Science, 30(5), pp. 719-726. (Year: 2012).*
Elzoghby et al., Journal of Controlled Release, 157, pp. 168-182. (Year: 2012).*
Varga et al., "BSA/polyelectrolyte core-shell nanoparticles for controlled release of encapsulated ibuprofen", Colloid Surf. B: Biointerfaces 123 (2014) 616-622.
Xie et al., "Bovine serum albumin nanoparticles modified with multilayers and aptamers for pH-responsive and targeted anticancer drug delivery", J. Mater. Chem. (2012) 22: 6053-6060.
Mendoza-Dorantes et al., "Encapsulation and surface charge manipulation of organic and inorganic colloidal substrates by multilayered polyelectrolyte films", Colloids and Surfaces: Physiochem. Eng. Aspects (2013) 434: 253-259.
Singh et al., "Human serum albumin nanoparticles for enhanced drug delivery to treat breast cancer: Preparation and in vitro assessment", Int. J. of Pharm. & Life Sci. (2012) 3(10): 2055-2063.
Szarpak et al., "Multilayer Assembly of Hyaluronic Acid/ Poly(allylamine): Control of the Buildup for the Production of Hollow Capsules", Langmuir 2008, 24, 9767-9774.
Lehne, "P-glycoprotein as a Drug Target in the Treatment of Multidrug Resistant Cancer", Current Drug Targets, 1 (2000) 85-99.
Black et al., "Modulation of Brain Tumor Capillaries for Enhanced Drug Delivery Selectively to Brain Tumor", Cancer Contr, 11 (2004) 165-173.
Oláh et al., "Unexpected effects of peripherally administered kynurenic acid on cortical spreading depression and related blood-brain barrier permeability", Drug Design, Development and Therapy 7 (2013) 981-987.

(Continued)

*Primary Examiner* — Abigail Vanhorn
(74) *Attorney, Agent, or Firm* — Jason D. Voight

(57) ABSTRACT

The present invention relates to nanocomposites for the controlled delivery of active ingredients into the central nervous system. The nanocomposite according to the present invention comprises a biocompatible core part comprising biodegradable material, and polyelectrolytes able to form a electrostatic van der Waals interactions with the material of the core part. The core part of the nanocomposite is able to bind various pharmaceutical agents. The present invention also relates to a process for the preparation of the nanocomposite according to the present invention and to the use of the nanocomposite according to the present invention.

12 Claims, 7 Drawing Sheets

(56) References Cited

OTHER PUBLICATIONS

Füvesi et al., "Comparative study on the effects of kynurenic acid and glucosamine-kynurenic acid", Pharmacology, Biochemistry and Behavior 77 (2004) 95-102.

Nagy et al., "Synthesis and biological effects of some kynurenic acid analogs", Bioorg. Med. Chem. 19 (2011) 7590-7596.

Battaglia et al., "Systemically administered D-glucose conjugates of 7-chlorokynurenic acid are centrally available and exert anticonvulsant activity in rodents", Brain Research 860 (2000) 149-156.

Wennström et al., "Kynurenic Acid Levels in Cerebrospinal Fluid from Patients with Alzheimer's Disease or Dementia with Lewy Bodies", International Journal of Tryptophan Research 7 (2014) 1-7.

Hornok et al., "Preparation and properties of nanoscale containers for biomedical application in drug delivery: preliminary studies with kynurenic acid", J Neural Transm (2012) 119:115-121.

López et al., "Preparation and Characterization of Kynurenic Acid Occluded in Sol-Gel Silica and SBA-15 Silica as Release Reservoirs", Journal of Nanomaterials, 2014, 1-8.

Mannila, "Central Nervous System Permeation of Ibuprofen, Ketoprofen and Indomethacin—doctoral dissertation", University of Kupio, 2009.

Vatassery et al., "High doses of vitamin E in the treatment of disorders of the central nervous system in the aged", Am J Clin Nutr 1999; 70:793-801.

Pinnell, "Cutaneous photodamage, oxidative stress, and topical antioxidant protection", Journal of the American Academy of Dermatology 2003; 48:1-19.

Si-Shen Feng et al., "Poly(lactide)—vitamin E derivative/montmorillonite nanoparticle formulations for the oral delivery of Docetaxel", Biomaterials 30 (2009) 3297-3306.

Fischer et al., "Concurrent Administration of Water-Soluble Vitamin E Can Increase the Oral Bioavailability of Cyclosporine A in Healthy Dogs", Veterinary Therapeutics 3 (2002) 465-73.

Carroll et al., "Brain-targeted delivery of Tempol-loaded nanoparticles for neurological disorders", Journal of Drug Targeting, 18 (2010) 665-674.

Danhier et al., "Vitamin E-based micelles enhance the anticancer activity of doxorubicin", International Journal of Pharmaceutics 476 (2014) 9-15.

Langer et al., "Optimization of the preparation process for human serum albumin (HSA) nanoparticles", Int. J. Pharm. 257 (2003) 169-180.

Varga et al., "BSA/polyelectrolyte core-shell nanoparticles for controlled release of encapsulated ibuprofen", Colloids and Surfaces B 123 (2014) 616-622.

Gelamo et al., "Interaction of bovine (BSA) and human (HSA) serum albumins with ionic surfactants: spectroscopy and modelling", Biochimica et Biophysica Acta 1594 (2002) 84-99.

Hirayama et al., "Rapid confirmation and revision of the primary structure of bovine serum albumin by ESIMS and Frit-FAB LC/MS", Biochem Biophys Res Commun, 173 (1990) 639-646.

Hua-Li Yue et al., "Green synthesis and physical characterization of Au nanoparticles and their interaction with bovine serum albumin", Colloids and Surfaces B:Biointerfaces 122 (2014) 107-114.

Rub et al., "Study on the interaction between amphiphilic drug and bovine serum albumin: A thermodynamic and spectroscopic description", Journal of Luminescence 155 (2014) 39-46.

B.K. bozoğlan et al., "Investigation of neohesperidin dihydrochalcone binding to human serum albumin by spectroscopic methods", Journal of Luminescence 155 (2014) 198-204.

Di Wu et al., "Characterisation of interaction between food colourant allura red AC and human serum albumin: Multispectroscopic analyses and docking simulations", Food Chemistry 170 (2015) 423-429.

Chertow et al., "Poly[allylamine Hydrochloride] (RenaGel): A Noncalcemic Phosphate Binder for the Treatment of Hyperphosphatemia in Chronic Renal Failure", American Journal of Kidney Diseases, 29 (1997) 66-71.

Crisante et al., "Antibiotic delivery polyurethanes containing albumin and polyallylamine nanoparticles", European Journal of Pharmaceutical Sciences 36 (2009) 555-564.

Molina-Boívar et al., "Spectroscopic investigation on the interaction of maslinic acid with bovine serum albumin", Journal of Luminescence 156 (2014) 141-149.

\* cited by examiner

SUSTAINED RELEASE NANOCOMPOSITE, A PROCESS FOR PRODUCING THE SAME AND USE THEREOF

This is the national stage of International Application PCT/HU2016/050034, filed Jul. 28, 2016.

The solution according to the present invention relates to nanocomposites, which are useful for the controlled delivery of active ingredients into the central nervous system. The nanocomposite according to the present invention comprises a core part comprising biocompatible and biodegradable material, and polyelectrolyte able to form a chemical bond with the material of the core part. The core part of the nanocomposite is able to bind various pharmaceutical agents. The subject matter according to the present invention also relates to a process for the preparation of the nanocomposite according to the present invention and to the use of the nanocomposite according to the present invention.

The invention relates to the preparation of a core-shell nanoparticle, which comprises an active ingredient with a neuroprotective effect, kynurenic acid (KYNA), dopamine (DOPA), or a non-steroidal anti-inflammatory agent, ibuprofen (IBU). At the same time the encapsulation technology achievable on a nanometric scale makes the controlled rate penetration of the active ingredient possible through certain biological structures. The success of the synthesis is demonstrated by the active ingredient penetrating through the blood-brain barrier by means of the nanocomposite with core-shell structure. Thus the invention relates to an active ingredient molecule bound to a biocompatible protein, which, being surrounded by a polyelectrolyte shell on a nano-size, can cross the blood-brain barrier (BBB) in a suitable concentration. Furthermore, the structure of the core-shell composite ensures the controlled release of the active ingredient (the release of the active ingredient) within physiological circumstances.

THE STATE OF THE ART

Controlled Release Systems

In pharmacological research it is insufficient simply to synthetically prepare a drug, it is also important to deliver the active ingredient in the acceptable concentration to the target location, as well as the achievement of the controlled and targeted release of the active ingredient. Accordingly, the purpose of prolonged release systems is to satisfy the needs relating to the amount of a given dose at the target location, as well as the duration of the release. The release in the organism may proceed both through a physical, and a chemical route. There are pH-sensitive gels, which open to a specific pH, thus releasing the active ingredient, or biodegradable polymer, whose hydrolysis causes the active ingredient to release. There are also systems, which activate by a biochemical route (by enzymes or in biological processes), and as a consequence of this the drug molecule exerts its effect. The release may be effected both as a result of an external impact, or automatically, for example by diffusion, which may be controlled by the formation of one or more layers around the active ingredient. These systems are in all cases of nano- or micrometer magnitude, which prevent the premature degradation or rapid release of the drug molecules. The shell-controlled release can be maintained for hours, for several days, several weeks, or even several months. An additional benefit of the prolonged release of active ingredients is that the active ingredients will not appear suddenly in too large amount in the organism, thereby the organism will not treat it as unknown material and it will not be excreted without use. The core-shell capsules enabling the controlled release of the active ingredient are known from the literature, however, due to their size they are not suitable to deliver active ingredient into the central nervous system (Szarpak et al. Multilayer Assembly of Hyaluronic Acid/Poly(allylamine): Control of the Buildup for the Production of Hollow Capsules. *Langmuir* 2008, 24, 9767-9774).

For biological application, besides the size, it is very important that the constituents of the system consist of biodegradable materials, do not cause aggregation, or do not induce any other process, which is harmful for the organism. Therefore proteins, micelles, liposomes, or materials, which themselves are available in the organism, (e.g. lipides), or tissue constituents (e.g. hyaluronic acid) or even a cell, into which the drug molecules can be encased and incorporated in the organism, are often used. The conjugates such formed are packaged by materials of similar nature, elaborating a core-shell structure. The materials used for the shell may be of various kind: inorganic nanoparticles, lipids, biopolymers, or even polyelecrolites. Among the latter the use of PLGA (poly(lactic-co-glycolic acid)) is very widespread, as it decomposes to lactic acid and glycolic acid by its hydrolysis, or the use of chitosan, which is a known anti-bleeding agent, which is also used for the regeneration of tissues.

For the treatment of a number of diseases it is insufficient to discover the suitable active ingredient, it remains without effect due to the fact that it is unable to reach the desired area. The problem mostly affects the area "closed" by the blood-brain barrier, the central nervous system (CNS). An important element of the blood-brain barrier is constituted by the endothelic cells closely fitting to each other. Other important elements of the blood-brain barrier are the astrocytes closely fitted to the external surface of the capillaries, as well as the pericytes. These together ensure the barrier function, the protection of the brain as a structural and enzymatic barrier. Overcoming this problem is extremely important in the treatment of diseases of the CNS, e.g. brain tumours, infections, neurodegenerative diseases (e.g. Alzheimer's and Parkinson's disease, amyothrophic lateral sclerosis, multiple sclerosis) or for example in the treatment of migraine and epilepsy. The blood-brain barrier has important functions, as it provides an effective protection against harmful materials, however, the small molecules can easily cross it (oxygen, ethanol, carbon dioxide).

Therefore the precondition of the diffusion of drugs from the blood into the brain is the penetration of the lipid membrane. To achieve this, indispensable conditions are the hydrophobic character and the small size. A number of pharmacons do not possess these features, thus various technical solutions must be applied to overcome the problem. Originally such processes were applied, in which mannitol was injected in the neck artery, and as a result of this the routes opened for the free inflow of the active compound. This, however has a number of side effects, for example physiological stress, increased intracranial pressure, the delivery of undesired materials into the brain, the delivery of drugs into the normal tissues (G. Lehne, *Current Drug Targets*, 1 (2000) 85-99; K. L. Black and N. S. Ningaraj, *Cancer Contr*, 11 (2004) 165-173). Further solutions were invented to overcome the problem, however, their drawbacks could not be eliminated, and therefore a new approach was believed to be discovered in the development of drug carriers with a colloid size range. The requirements to be met by these solutions were as follows: the particle size be ≤100 nm, they must not be toxic, they must be stable in the blood, they must not aggregate, the RHS (reticulohistiocyte system) should not remove them, they should remain in the blood for long, furthermore, they should be cost effective, and their production should be simple. To date, none of the materials could meet these requirements alone.

An alternative solution for overcoming of the problem of crossing the blood-brain barrier by an active ingredient may be presented by the development of nano-carrier systems in order that they carry the drugs. These nano-sized systems possess a number of advantages, for example they can be bound to a given area by a suitable functionalization in order to achieve the targeted release of an active ingredient. Their further benefit is that the use of smaller amount of active compound is sufficient, the chemical and enzymatic degradation of the drug can be prevented during their delivery to the suitable location, the controlled release of the active ingredient can be achieved, furthermore, a number of mode of administration is possible (oral, parenteral, inhalation, etc.).

A number of pharmaceutically active ingredients are known, whose target point can be found in the central nervous system, however, either the blood-brain barrier, or the peripheral metabolism, for example an enzymatic degradation of the active ingredient prevents the meeting of the active ingredient and the target molecule. In other cases, though the active ingredient enters the brain, however in order to achieve the effective concentration the administration of very large doses is necessary. It is known, for example, that the N-methyl-D-aspartate (NMDA) receptor antagonist kynurenic acid (KYNA) hardly crosses the blood-brain barrier, while its precursor, L-kynurenine can enter the brain (S. Fukui and et al., J Neurochem. 56 (1991) 1471-4159; G. Oláh and et al., Drug Design, Development and Therapy 7 (2013) 981-987). G. Battaglia et al. synthetized glucose-KYNA conjugates, which resulted such a successful delivery to the brain, as it was measured for an analogue of KYNA, the 7-chloro-KYNA molecule (BrainRes., 860 (2000) 149-156). Another functionalization was presented by the modification of KYNA by glucosamine, as a result of which although the KYNA and the conjugate gave similar results, however, the conjugate with glucosamine more easily crosses the BBB (J. Rivesi, Pharmacology, Biochemistry and Behavior 77 (2004) 95-102). K. Nagy and Fülöp et al. managed to synthesize a more effective KYNA derivative, said material administered peripherally, exerted a neuroprotective effect as a consequence of its crossing through the blood-brain barrier (K. Nagy and et al., BioorgMedChem 19 (2011) 7590-7596; F. Fülöp and et al., J NeuralTransm. 119 (2012) 109-114).

The significant increasing of the concentration of KYNA in the brain may cause various neurological signs of disorder, cognitive changes (M. Wennström, International Journal of Tryptophan Research 7 (2014) 1-7). The kynurenic acid encased in a micelle offers an opportunity to maintain the concentration of the active compound at a certain level in the brain. As a result of this experiment significant amount of KYNA was incorporated by the central nervous system, while the KYNA without micelle did not cause any change during the in vivo studies (V. Hornok, J NeuralTransm 119 (2012) 115-121).

For the encapsulation of KYNA a solution may be offered by the packaging of KYNA. This was studied by López et al. applying various silica carriers (T. López and et al., Journal of Nanomaterials, (2014) http://dx.doi.org/10.1155/2014/507178). It has been demonstrated that the structure of KYNA had not been modified during the binding to the silica. Based on the in vivo experiments, the dissolution from the hexagonal structure was very slow (20 percent, in 24 hours), however in viva experiments have not been made.

Dopamine (DOPA) is a very important neurotransmitter, having an outstanding role in the treatment of Parkinson's disease, however, its application presents a similar problem to be solved, as it has been seen in the case of KYNA. The precursor of DOPA, L-DOPA (levodopa) can cross the blood-brain barrier, then it converts to dopamine in the brain by decarboxylation. However, the peripheric decarboxylases metabolize the majority of the levodopa administered systematically before it would reach the central nervous system at all. The effective concentration of the externally administered dopamine in the brain therefore can only be ensured by the co-administration of peripheric decarboxylase inhibitors, and by administration of a higher dose than it would otherwise be necessary.

The non-steroidal anti-inflammatory agents are the most frequently used active ingredients, which are generally known to be able to enter the CNS, however, to date there is insufficient information about the mechanism of the entrance of the active compound. On the other hand, their peripheral effects are well known, therefore the understanding of their incorporation by the CNS, and their dispersing in the CNS is a very important task. Furthermore, in case of adults and the elder, the long term use of these agents reduces the risk of the development of neurodegenerative diseases, or delays the development of neurodegenerative diseases (such as, e.g. Alzheimer's disease) (Anne Mannila, *Central Nervous System Permeation of Ibuprofen, Ketoprofen and Indomethacin—doctoral dissertation,* 2009).

In case of chronically administered pharmaceutically active ingredients exerting effect in the central nervous system it is especially important to minimize the peripheral side effects, for example by the controlled release of the active ingredient, and the decrease of the dose.

Besides the active ingredients, it may be necessary to administer into the CNS compounds that facilitate the effect of the active ingredients, which are optionally bound to the active ingredient molecule. These compounds, similarly to the active ingredient molecule, may be such that cannot cross the blood-brain barrier without appropriate formulation, or such that can be prepared in a form that can enter the central nervous system. Such a compound exerting an adjuvant effect is for example vitamin E. It is generally known that neuropathological changes may also happen in the central nervous system, if there is insufficient concentration of vitamin E in the brain. Although the number of the patients suffering from the lack of vitamin E is low, the defeating of the diseases causing thereof (e.g. liver, bile and intestinal diseases, furthermore, in the central nervous system: the dysfunction of the cerebellum, coordination disorders, etc.) is especially important challenge (G. T Vatassery et al., *Am. J. Clin. Nutr.* 70 (1999) 793-801). Vitamin E is an antioxidant, which binds the free radicals, which generate a number of change within the cells, impair the cell membranes, proteins, as well as the nucleic acids. The α-tocopherol (vitamin E) functions as a protection system, prevents the oxidative stress, and the lipid-solubility, which thus especially important in the protection of the cell membranes (R. Sheldon 48 (2003) 1-22). The vitamin crosses the blood-brain barrier, however orders of magnitude higher amount must be administered into the brain in order to increase the level systematically. The application of vitamin E, especially bound to polyethylene glycol, is beneficial not only for the reason of its above-mentioned positive effects. It demonstrates 67 times better effect in case of production emulsions as the polyvinyl alcohol, furthermore, it increases the biological availability of certain immunosupressors (ciklosporin A), antibiotics (vancomicin), furthermore beta blockers (tolinolol) (S.-S. Feng et al., *Biomaterials* 30 (2009) 3297-3306; J Fischer et al., *VeterinaryTherapeutics* 3 (2002) 465-73). The generation of reactive oxygen, and nitrogen radicals increases the risk of development of neurodegenerative diseases, therefore the application of tocopherol seems to be useful for the binding of such radicals, and the treatment of the disease (R. T Carroll, *Journal of DrugTargeting*, 18 (2010) 665-674).

As another opportunity in the literature, an anti-cancer agent (doxorubicin) is enclosed in the internal part of the vitamin E micelle, in order to develop a more effective chemotherapy F. Danhier. *International Journal of Pharmaceutics* 476 (2014) 9-15).

The literature describes composites suitable for the administration of pharmaceutically active ingredients, and the components thereof. As a carrier, e.g. bovine serum albumin (BSA) may be applied, which is a biocompatible, biodegradable macromolecule, which possesses a very beneficial side effect profile (K. Langer and et al., *Int. J. Pharm.* 257 (2003) 169-180). Its application is extremely widespread due to its known structure, and ligand-binding characteristics (J. A. Molina-Bolivar, *Journal of Luminescence* 156 (2014) 141-149; N Varga and et al., *Colloids and Surfaces B* 123 (2014) 616-622). BSA is a protein with 66500 Da molecular weight, which is composed of 583 amino acids, its structure is stabilized by 17 disulphide bridges, and contains 2 triptophane groups, which makes the fluorimetric investigation possible (E. L. Gelamo and et al., *Biochimica et BiophysicaActa* 1594 (2002) 84-99; K Hirayama and et al., *Biochem Biophys Res Commun,* 173 (1990) 639-646). Proteins, e.g. BSA, due to their structure, may beneficially be applied for the binding of the pharmaceutically active ingredient.

The proteins take various conformations depending on the pH of the solvent, their secondary structure changes due to this factor. Thus, a protein in native (N) state contains almost to 55% α-helix structure. However, at higher or lower pH, the α-helix content of the protein decreases, thus, at e.g. pH=3 it is ~35%, at pH~4.4 it is ~45%, while at pH=8, and at pH=10 it is approximately 48% in both cases (J. F. Foster (1977) 53-84, *Pergamon Press*, New York). A number of publications have been published about the fact that the changes in the structure may be caused not only by the pH, but also the ligands bound to the protein. The changes developing in the secondary structure of the proteins are basically investigated by CD spectroscopy. Noble metal nanoparticles, e.g. gold may also induce a disorder in the structure of the protein, which may be accompanied by the unfolding of the protein chains, the changing of the integrated structure (H. L. Yue and et al., *Colloids and Surfaces B:Biointerfaces* 122 (2014) 107-114). The interaction of the protein with certain kind of pharmaceutically active molecule, furthermore the studying of the structural change caused by the drug are very substantial pieces of information from the point of view of the biological application. Accordingly, a number of publications deal with the investigation of this topic (M. A. Rub and et al., *Journal of Luminescence* 155 (2014) 39-46; B. K. Bozoglan, *Journal of Luminescence* 155 (2014) 198-204).

The negative band appearing at 208 nm of the signal provided by the CD spectra gives information about the α-helix content of the protein. The MRE value (Mean Residue Ellipticity): may be calculated from the signal received according to the following formula: $MRE=\theta_{obs}/(c_p*n*1*10)$, wherein $\theta_{obs}$, stands for the measured CD signal, $c_p$ stands for the molar concentration of the protein, n stands for the number of amino acids, 1 stands for the length of the route. The α-helix content may be calculated on the basis of the MRE-value: α-helix $\%=[(-MRE_{208}-4000)/(33000-4000)]*100$, wherein $MRE_{208}$ stands for the MRE value given at 208 nm, 4000 stands for the MRE value belonging to the α- and random coil conformation at 208 nm, furthermore 33000 stands for the MRE value characteristic to the pure α-helix structure at 208 nm (B. K. Bozoglan, Journal of Luminescence 155 (2014) 198-204; D. Wu and et al., *Food Chemistry* 170 (2015) 423-429).

There are compounds known from the literature which, linking to the carrier, can improve the physicochemical characteristics of the pharmaceutically active ingredient-carrier complex, or modify the biological activity thereof. Poly-(allylamine hydrochloride) (PAH) is a biocompatible synthetics polycation, which is presently also used in the medical practice as phosphate binder; for the treatment of chronic renal insufficiency (hyperphosphatemia) (G. M. Chertow, American Journal of Kidney Diseases, 29 (1997) 66-71; F. Crisante, European Journal of Pharmaceutical Sciences 36 (2009) 555-564). Similar compounds are as follows: poly-(sodium 4-styrene-sulfonate) (PSS), chitosan (Chit), poly-(L-lysine) (PLL), alginate.

BRIEF DESCRIPTION OF THE INVENTION

Figure 1:
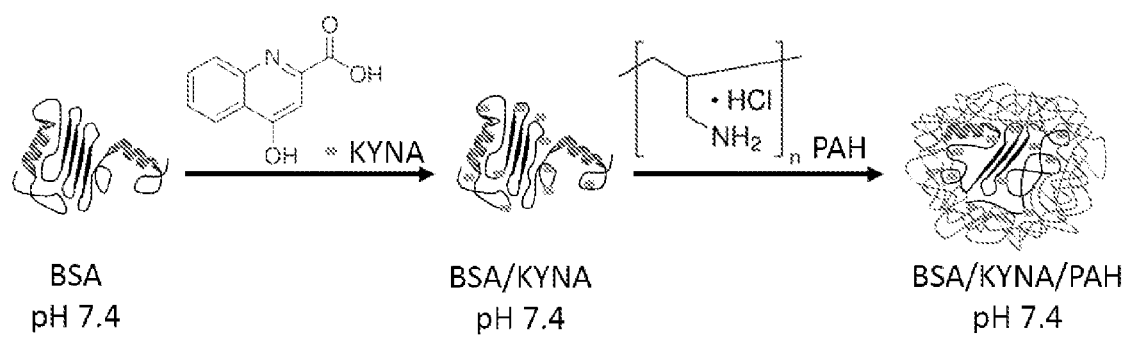
FIG. 1: A schematic figure about the synthesis of the core-shell nanocomposite.

The solution according to the invention will be disclosed in the following sections.

1. Nanocomposite of an active ingredient for the controlled release into the central nervous system, and/or for decreasing the peripheric side effects of the active ingredients, said nanocomposite comprises
   a) a core-part, which comprises a biocompatible, biologically degrading material, which can reversibly bind the active ingredients and release them at a target area, wherein the concentration of the biocompatible, biodegradable material in the core is 4-30 w/v %, and the diameter of the core is 5-10 nm;
   b) one or more shell-part, which comprises a polyelectrolyte, which can form a chemical bond with the material of the core-part, and optionally one or more other biocompatible material, wherein the concentration of the polyelectrolyte in the shell-part is 0.04-1.5 w/v %, characterized in that the core-part and the shell-part are linked to each other by a chemical bond.

2. The nanocomposite as disclosed in Section 1, wherein the a) core-part comprises a material selected from the group as follows: an albumin, preferably human serum albumin (HSA), bovine serum albumin (BSA), and a lysozyme, wherein said materials are preferably present in native form; and/or the b) shell-part as polyelectrolyte comprises poly-(allylamine hydrochloride) (PAH), and/or the b) shell-part comprises a material selected from the group as follows: hyaluronic acid, poly-(lactic-co-glycolic acid), poly-(sodium-4-styrene sulfonate) (PSS), chitosan (Chit), poly-(L-lysine) (PLL), alginate.

3. The nanocomposite as disclosed in Sections 1 or 2, wherein
   the a) core-part comprises bovine serum albumin (BSA);
   the b) shell-part comprises poly-(allylamine hydrochloride) (PAH) as a polyelectrolyte, characterized in that, the hydrodynamic diameter of the nanocomposite is d=20.5 nm (SD=±1.2 nm), measured with a HORIBA SZ-100 type dynamic light scattering measuring device, zeta potential is $\zeta$=−2.8 mV (SD=±0.2 mV), and the diameter of the core determined by SAX measuring, using a Philips, PW-1830 equipment is D=12.5 nm (SD=±0.3 nm).

4. The nanocomposite as disclosed in Sections 1 or 2, further comprises one or more active ingredients, preferably selected from the following group: kynurenic acid (KYNA), sodium kynurenate, dopamine (DOPA), ibuprofen (IBU); and/or an adjuvant facilitating the crossing of the active ingredient through the blood-brain barrier, preferably vitamin E.

5. The nanocomposite as disclosed in Section 4, characterized in that it possesses the following sizes and structural characteristics:
   a) when the nanocomposite comprises bovine serum albumin and kynurenic acid: the hydrodynamic diameter of the nanocomposite is d=103.4 nm (SD=±4.8 nm), measured with a HORIBA SZ-100 type dynamic light scattering measuring device, the zeta potential is $\zeta$=−6.5 mV (SD=±0.3 mV), and the diameter of the core determined by SAX measuring, using a Philips, PW-1830 equipment is D=10.2 nm (SD=±0.3 nm);
   b) when the nanocomposite comprises bovine serum albumin and dopamine: the hydrodynamic diameter of the nanocomposite is d=101.9 nm (SD=±5.3 nm), measured with a HORIBA SZ-100 type dynamic light scattering measuring device, the zeta potential is $\zeta$=−7.1 mV (SD=±0.3 mV), and the diameter of the core determined by SAX measuring, using a Philips, PW-1830 equipment is D=11.1 nm (SD=±0.4 nm);
   c) when the nanocomposite comprises bovine serum albumin and ibuprofen: the hydrodynamic diameter of the nanocomposite is d=99.8 nm (SD=±2.5 nm), measured with a HORIBA SZ-100 type dynamic light scattering measuring device, the zeta potential is $\zeta$=−6.8 mV (SD=±0.4 mV), and the diameter of the core determined by SAX measuring, using a Philips, PW-1830 equipment is D=10.5 nm (SD=±0.1 nm).

6. Process for the preparation of the nanocomposite as disclosed in Sections 1 to 5, characterized in that, the following steps are performed:
   a) the polymer constituting the core-part is prepared in native conformation, with a diameter of 5-10 nm;
   b) a reversible interaction is formed between the core-polymer and the active ingredient in an aqueous media or in an appropriate buffer;
   c) the polyelectrolyte constituting the shell-part is added to the core as prepared in step b), comprising the core-polymer and the active ingredient;
   wherein the preparation of the nanocomposite takes place within a physiological environment, at pH between 6.5 and 7.5.

7. The nanocomposite as disclosed in any of Sections 1 to 5 for the controlled release of the active ingredients into the central nervous system, and/or for decreasing the peripheric side effects of the active ingredients.

8. The nanocomposite as disclosed in any of Sections 1 to 5 for the controlled release of the following active ingredients into the central nervous system, and/or for decreasing the peripheric side effects of said active ingredients: neurotransmitters, preferably kynurenic acid or its pharmaceutically acceptable salt, preferably sodium kynurenate, dopamine; a none-steroidal anti-inflammatory agent, preferably ibuprofen; vitamins, preferable vitamin E.

9. Use of the nanocomposite as disclosed in any of Sections 1 to 5 for the preparation of a pharmaceutical composition.

DETAILED DESCRIPTION OF THE INVENTION

New types of nanocomposites have been prepared within physiological conditions, in the nano-size range for the purpose of crossing the pharmaceutically active ingredients through the blood-brain barrier. The empty (not containing an active ingredient) composite as reference, furthermore the nanocomposites without shell, and those with one layer core-shell were characterised by various physico-chemical methods. The amount of the material constituting the composites, than the conditions of the preparation were determined. Stability studies were performed for the active ingredients by ensuring various conditions (pH=3 to 8 in physiological solution and without said physiological solution, in both phosphate and HEPES buffers). The results are demonstrated in Table 1.

TABLE 1 the stability study of KYNA in MQ, with 150 mM NaCl, and without NaCl, in PBS and HEPES buffer.

| pH | 0 h | 24 h | 48 h | 72 h | 96 h |
|---|---|---|---|---|---|
| 3 (MQ) | stable | stable | stable | stable | unstable |
| 4 (MQ) | stable | stable | stable | unstable | unstable |
| 5 (MQ) | stable | stable | stable | stable | unstable |
| 6 (MQ) | stable | stable | stable | unstable | unstable |
| 7 (MQ) | stable | stable | stable | unstable | unstable |

TABLE 1-continued the stability study of KYNA in MQ, with 150 mM NaCl,
and without NaCl, in PBS and HEPES buffer.

| pH | 0 h | 24 h | 48 h | 72 h | 96 h |
|---|---|---|---|---|---|
| 8 (MQ) | stable | stable | stable | stable | unstable |
| 3 (MQ + 150 mM NaCl) | stable | stable | stable | stable | unstable |
| 4 (MQ + 150 mM NaCl) | stable | stable | stable | stable | unstable |
| 5 (MQ + 150 mM NaCl) | stable | stable | unstable | unstable | unstable |
| 6 (MQ + 150 mM NaCl) | stable | stable | stable | stable | unstable |
| 7 (MQ + 150 mM NaCl) | stable | stable | stable | stable | unstable |
| 8 (MQ + 150 mM NaCl) | stable | stable | stable | stable | unstable |
| HEPES (150 mM NaCl) | stable | unstable | unstable | unstable | unstable |

Figure 6:
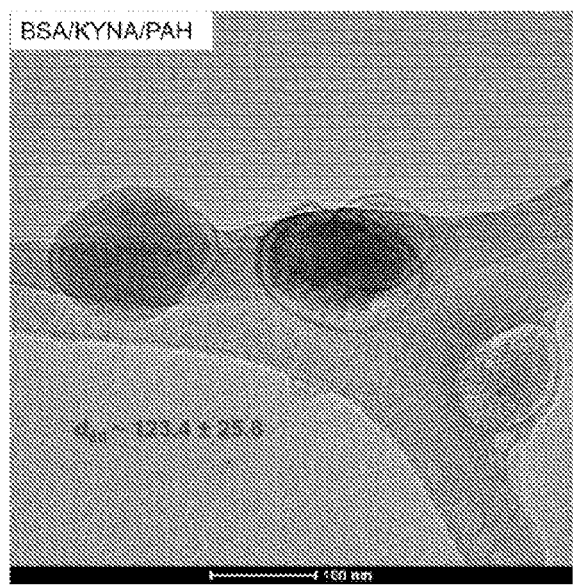
FIG. 6: A TEM image about the BSA/KYNA/PAH nano-core-shell composites (500× dilution).—

Based on the results the KYNA can be studied at room temperature, in MQ-water (type 1 laboratory purity water) within physiological conditions for several days. As a result of the buffers, the degrading of the KYNA already starts in the first hours, thus it is not recommended to investigate in buffer. Based on the results, the synthesis was accomplished in MQ with physiological saline solution, by setting the pH. Henceforth the detailed results of the studies of the core-shell nanocomposite prepared with KYNA will be demonstrated. The preparation of the corresponding composite (FIG. 1) was accomplished with the following parameters. The synthesis took place at room temperature, within physiological conditions, at pH=7.4, at constant ion-strength (0.9% NaCl). At a neutral pH the compact structure of the protein offers an opportunity to enclose large amount of kynurenic acid. In the "heart shaped" conformation of the BSA, the hydrophobic parts directed inside the conformation can form hydrogen-bridge, hydrophobic, furthermore $\pi\pi$ interactions with the KYNA molecule. The active ingredients added in large amount (1:175) to the protein can bind to the surface of the protein by its hydrophilic part, thereby binding to the hydrophobic parts of KYNA the polyelectrolyte will cover the BSA/KYNA composite. The formation of the core-shell composite is demonstrated by an electron microscopic image about the BSA/KYNA/PAH composite at 500-fold dilution (FIG. 6). With this packaging we can achieve the control of the release, furthermore the crossing of the active ingredient through the blood-brain barrier. Based on the in vitro experiments performed at 25 and 37.5° C. it can be demonstrated that the release of the KYNA by applying the core-shell composite is a well controlled process. After the in vitro drug release experiments the KYNA permeability was investigated with the help of an in vitro blood-brain barrier model. On the basis of the model the permeability coefficient of KYNA from the BSA/KYNA/PAH was significantly (1.9 times) higher compared to the permeability of the free KYNA. Based on these results it can be established that the KYNA crosses the blood-brain barrier in a lot larger amounts with the help of the BSA/KYNA/PAH nanocapsule, than does the free KYNA. After the positive results of the in vitro investigations, in vivo measurements were also performed. The animal experiments were performed on male Wistar rats (300 g, n=30). During the tests the effect of the peripherally administered KYNA was investigated in the central nervous system. Besides the control measurements the effect of KYNA, its precursor, L-kynurenin (L-KYN), the empty composite (BSA/PAH), furthermore the packaged KYNA (BSA/KYNA/PAH) respectively were measured.

Based on the results it can be established, that the packaging of KYNA was successful, measurable amount of KYNA entered the central nervous system through the blood-brain barrier. The signal measured during the regis-trated period of time refers to the fact, that KYNA not only crossed the blood-brain barrier, but also ensures the controlled release of the active ingredient.

Figure 2:
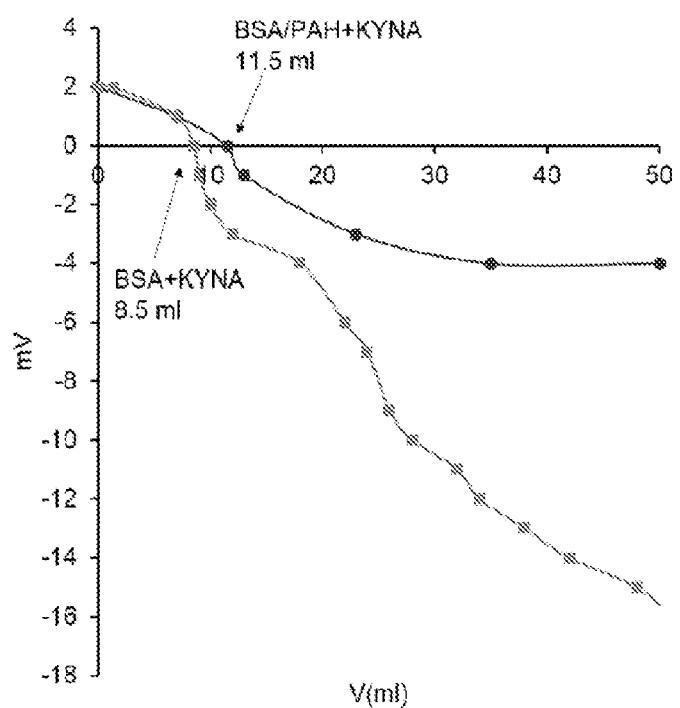
FIG. 2: The titration of the BSA (0.3% (g/100 cm$^3$)) and the BSA/PAH (0.42% (g/100 cm$^3$)) composite with KYNA (0.15% (g/100 cm$^3$)). As a result of the charge titration 410 mg, and 425 mg KYNA is necessary for the charge compensation of 1 g BSA, respectively.

The amount of BSA, furthermore the amount of the active ingredient required for the charge compensation of the BSA/PAH composite were determined by charge titration (FIG. 2). Based on the titration 410 mg and 425 mg KYNA is necessary to reach 1 g BSA 0 mV streaming potential value. Based on the result of the titration 500 mg KYNA was used in the synthesis.

Figure 3:
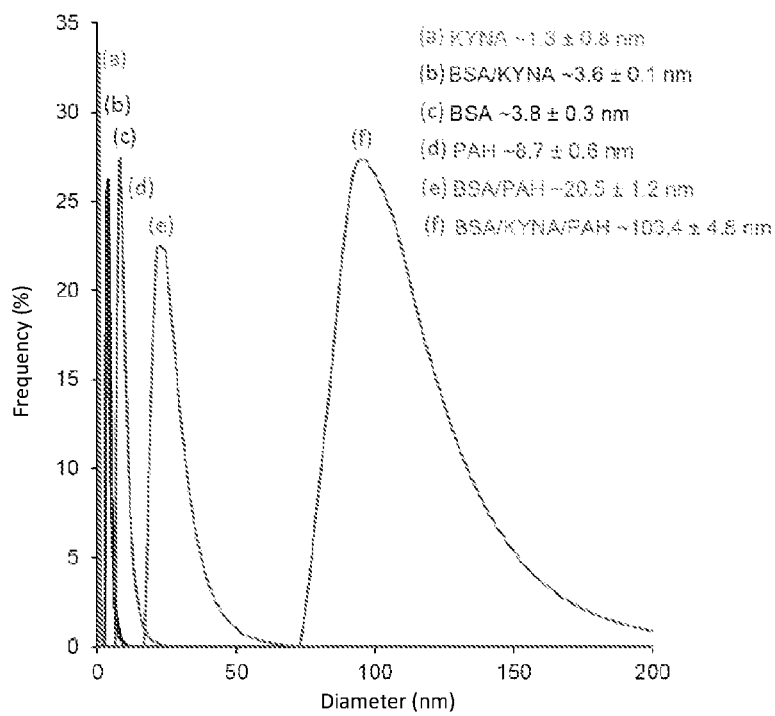
FIG. 3: Size distribution graphs about the starting materials, as well as the composites, indicating the sizes, furthermore their deviations.

The sizes of the protein (approx. 4 nm), the KYNA, the PAH (approx. 9 nm) the BSA/KYNA (approx. 20 nm), furthermore the BSA/KYNA/PAH (approx. 100 nm) composite were determined by dynamic lights scattering measurements (DLS). The size of the composites prepared at neutral pH falling into the nanometer range ensures the crossing of the blood-brain barrier by the active ingredients (FIG. 3).

The hydrodynamic diameters, furthermore the zeta potential were determined by a HORIBA SZ-100 type dynamic light scattering measuring device. The SAXS measurements (Philips PW-1830) were applied for the investigation of the internal structure of the core and the composites. Considering that this latter method investigates the size range corresponding to the reciprocal of this scattering vector, this can not be identical with the hydrodynamic diameters given by the light scattering measurements. The diameters determined by SAXS measurements thus relate only to the size of the protein (BSA). These data demonstrate that the active ingredients are incorporated in the internal structure of the protein.

TABLE 2

The sizes, zeta potentials of the composites on the basis of the dynamic light scattering measurements, and the sizes of the internal structure of the "core" based on the SAXS measurements

| | DLS | | | | SAXS | |
|---|---|---|---|---|---|---|
| | d (nm) | S.D. (±nm) | ζ (mV) | S.D. (±mV) | D (nm) | S.D. (±nm) |
| BSA | 3.8 | 0.3 | −1.1 | 0.2 | 8 | 0.2 |
| BSA/KYNA | 3.6 | 0.1 | −11.1 | 0.4 | 10.2 | 0.3 |
| BSA/KYNA/PAH | 103.4 | 4.8 | −6.5 | 0.3 | 15.5 | 0.5 |
| BSA | 3.8 | 0.3 | −1.1 | 0.2 | 8 | 0.2 |
| BSA/IBU | 3.7 | 0.4 | −11.6 | 0.2 | 10.5 | 0.1 |
| BSA/IBU/PAH | 99.8 | 2.5 | −6.8 | 0.4 | 16.2 | 0.2 |
| BSA | 3.8 | 0.3 | −1.1 | 0.2 | 8 | 0.2 |
| BSA/DOPA | 3.9 | 0.2 | −12.4 | 0.5 | 11.1 | 0.4 |
| BSA/DOPA/PAH | 101.9 | 5.3 | −7.1 | 0.3 | 18.5 | 0.5 |
| BSA/PAH | 20.5 | 1.2 | −2.8 | 0.2 | 12.5 | 0.3 |

Figure 4:
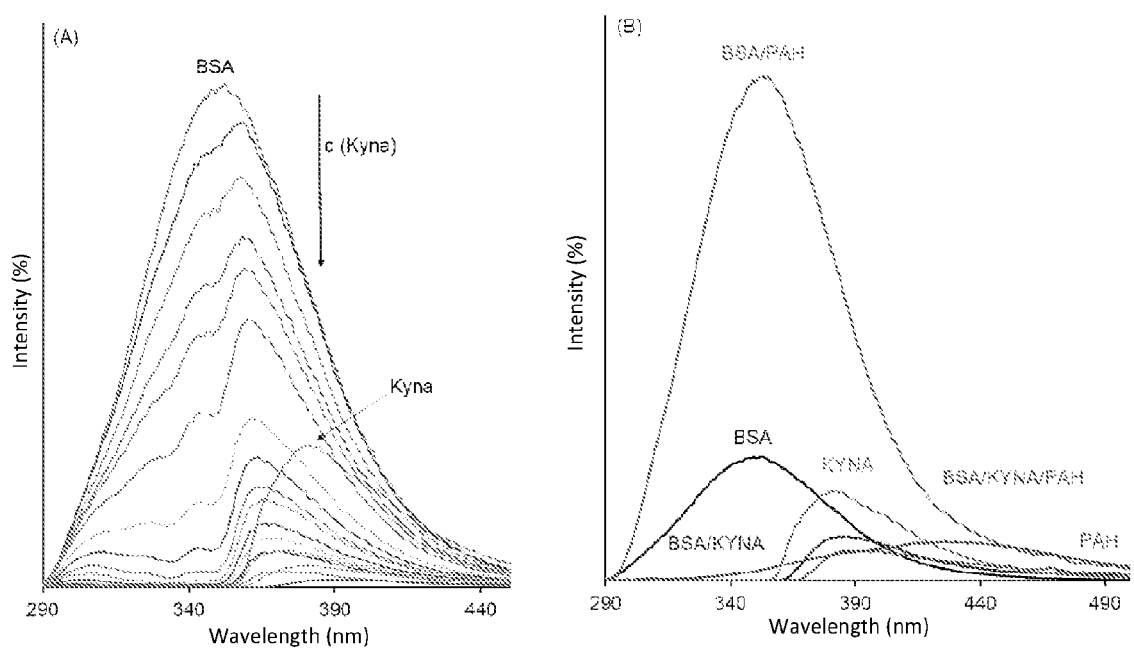
FIG. 4: (A) The change of the emission peak of the tryptophane with an increasing KYNA concentration ($c_{BSA}=0.075$ mM, $c_{KYNA}=0.011-13.22$ mM), (B) The emission of the starting materials and the composites in the amount of the synthesis.

Henceforth the changes of the emission of tryptophane that can be found in BSA were investigated using 280 nm excitation (FIG. 4). The emission peak can be found at 348 nm, which suggests that the tryptophane groups are exposed to the effects of the solvent, that is water, thereby the polarity of the cromophor groups changes, and the emission peak appears at a higher wavelength. With increasing KYNA concentrations this band permanently shifts towards higher wavelengths along with a continuous decrease in intensity. The shift goes until 383 nm, where the emission peak of the active ingredient is found. Thus the excess KYNA (BSA: KYNA=1:133) will shade the emission of tryptophane. The emission measured within the conditions of the synthesis demonstrated similar result. The emission intensity of the BSA/KYNA band appearing at 383 nm (1:175) decreases as a result of PAH, thus the polyelectrolyte covered the BSA/

KYNA composite. The chains of the protein without active ingredient will unfold as a result of PAH, which is demonstrated by the expressed increase of the emission intensity.

Figure 5:
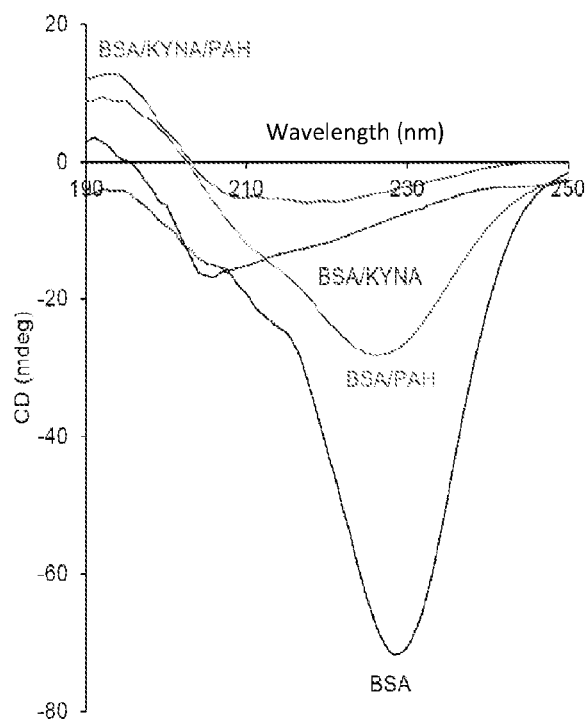
FIG. 5: CD-spectra about BSA, furthermore about the prepared composites at pH=7.4, in the range of 190-250 nm.

The change of the secondary structure of the protein was monitored by CD spectroscopy (FIG. 5). The protein present in its native form possesses the α-helix content identical with the literature data (~53%). In spite of the large excess, the binding of KYNA results in only slight decrease in the secondary structure of the protein (~52%). The polyelectrolyte causes significant perturbation in the structure, the α-helix content decreased to ~16%. Without active ingredient the PAH does not cause such a big change, the integrated structure decreases to ~30% in the protein.

The electron microscopic image of the one-layer BSA/KYNA/PAH composite (FIG. 6) demonstrates the development of the core-shell structure. By means of the ImageJ software the size has been established, where 123.4±25.8 nm was obtained.

Figure 7:
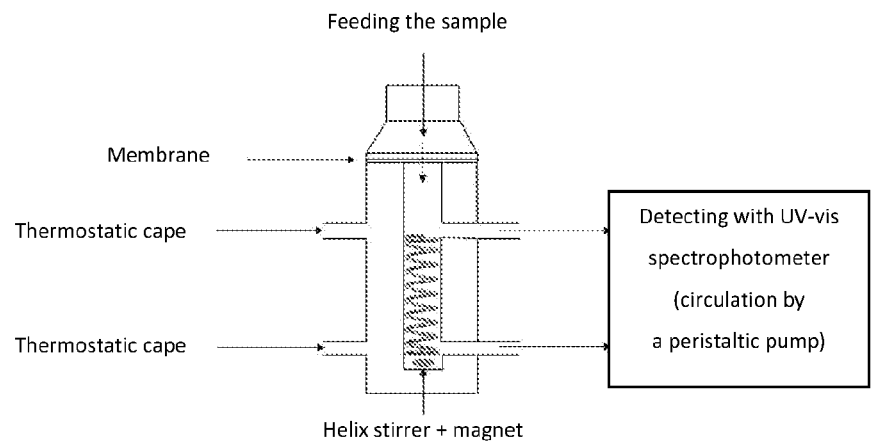
FIG. 7: A schematic figure of the Franz-cell (vertical diffusion cell) with which the in vitro drug release experiments were carried out.
Figure 8:
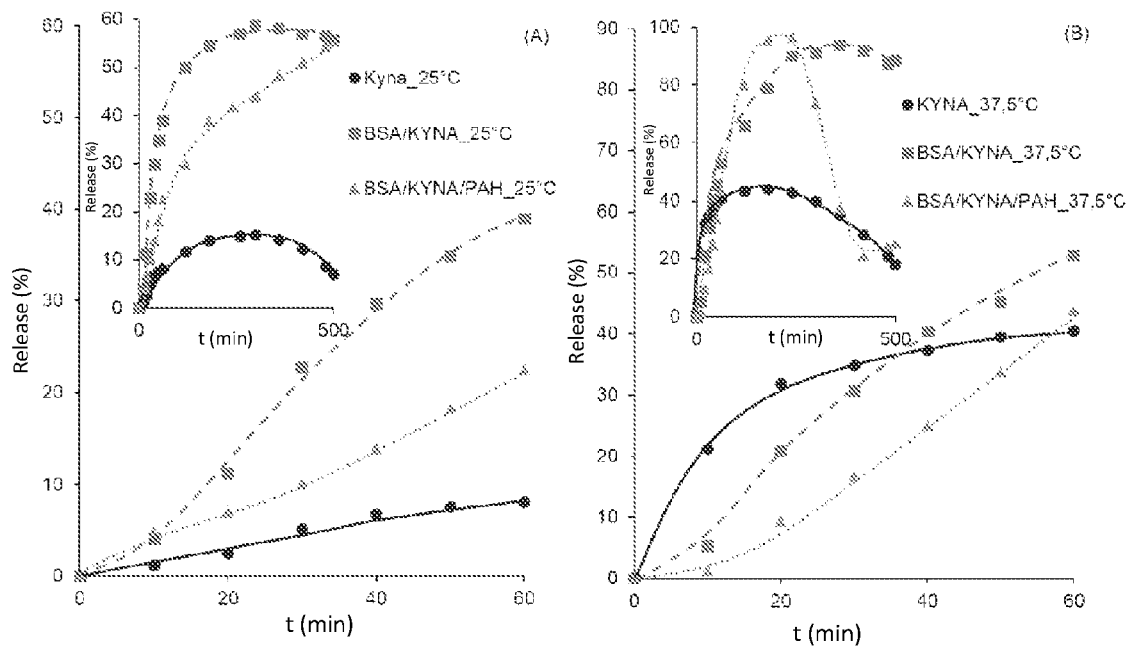
FIG. 8: The release profiles of KYNA at 25 and 37.5° C., respectively.

KYNA, within certain conditions, is a highly unstable compound, for example in a buffer (see: stability), or as a result of other external effects, for example the increase of the temperature, or as a result of light. The active ingredient release tests were made at two temperatures: at 25 and 37.5° C. (FIGS. 7 and 8). The experiments performed demonstrate, how the core-shell composite (BSA/KYNA/PAH) regulates the release as compared to the composite without a shell. The release kinetics can be concluded from the initial period.

Tables 3 to 5 contain the results obtained based on the kinetical models. The release of KYNA depends exclusively on the rate of diffusion through the membrane, which is characterized by the Higuchi model. The dissolution of an active ingredient from a composite without a shell is a procedure affected by concentration and diffusion, as it is stated by the first-order and the Higuchi model ($R^2 > 0.98$). A concentration-independent and well regulated dissolution is described by the zero-order rate model, which best fits the BSA/KYNA/PAH composite. Thus an active ingredient release system which is well regulated by the shell has been demonstrated. The values of the rate constants well demonstrate that the shell decreases the rate of dissolution; the release of the active ingredient from the BSA/KYNA/PAH composite is one magnitude slower than that is experienced in case of KYNA or BSA/KYNA.

Tables 3 to 5 contain the release rates calculated from the in vitro release profiles based on various kinetic models, in case of various active ingredients. The bolding indicates, which model fits which material or composite, that is which is the factor or parameter that most determines the dissolution of a given active ingredient.

It can be seen that in cases of the active ingredient or the BSA/active ingredient composite the release rate depends only on the diffusion ability of the active ingredient, in other words it depends only on the rate of diffusion through the membrane. In case of the one-layer composite the shell determines the rate of release, consequently, it does not depend on the active ingredient content of the composite, this is described by the zero-order rate model. In this case a well controlled active ingredient dissolution process takes place, which maintains constant active ingredient level in the blood stream in the biological systems.

TABLE 3

The release rates for KYNA containing composites on the basis of zero-order, first-order and Higuchi-model, respectively

| | Release rate Temperature | Not depending on the concentration zero-order $kd(s^{-1})$ | Depending on the concentration first-order $kd(s^{-1})$ | Diffusion controlled Higuchi $kd(s^{-1/2})$ |
|---|---|---|---|---|
| KYNA | 25° C. | $4.0 * 10^{-4}$ | $1.5 * 10^{-3}$ | **$4.9 * 10^{-3}$** |
| | 37.5° C. | $1.0 * 10^{-3}$ | $5.2 * 10^3$ | **$1.2 * 10^{-2}$** |
| BSA/KYNA | 25° C. | $1.6 * 10^{-3}$ | $9.4 * 10^{-3}$ | **$1.7 * 10^{-2}$** |
| | 37.5° C. | $2.4 * 10^{-3}$ | $1.4 * 10^{-2}$ | **$2.6 * 10^{-2}$** |
| BSA/KYNA/PAH | 25° C. | **$8.0 * 10^{-4}$** | $4.2 * 10^{-3}$ | $8.5 * 10^{-2}$ |
| | 37.5° C. | **$3.0 * 10^{-4}$** | $1.1 * 10^{-2}$ | $2.8 * 10^{-3}$ |

TABLE 4

The release rates for IBU containing composites on the basis of zero-order, first-order and Higuchi-model, respectively

| | Release rate Temperature | Not depending on the concentration zero-order $kd(s^{-1})$ | Depending on the concentration first-order $kd(s^{-1})$ | Diffusion controlled Higuchi $kd(s^{-1/2})$ |
|---|---|---|---|---|
| IBU | 25° C. | $5.0 * 10^{-1}$ | $6.4 * 10^{-3}$ | **$5.6 * 10^{-0}$** |
| | 37.5° C. | $7.7 * 10^{-1}$ | $1.1 * 10^{-2}$ | **$8.7 * 10^{-0}$** |
| BSA/KYNA | 25° C. | $6.5 * 10^{-2}$ | **$1.5 * 10^{-3}$** | $6.1 * 10^{-1}$ |
| | 37.5° C. | $2.2 * 10^{-1}$ | $2.3 * 10^{-3}$ | $2.4 * 10^{-0}$ |
| BSA/KYNA/PAH | 25° C. | **$5.2 * 10^{-2}$** | $7.0 * 10^{-4}$ | $5.4 * 10^{-1}$ |
| | 37.5° C. | **$1.3 * 10^{-1}$** | $1.5 * 10^{-3}$ | $1.4 * 10^{-0}$ |

TABLE 5

The release rates for DOPA containing composites on the basis of zero-order, first-order and Higuchi-model, respectively

| | Release rate Temperature | Not depending on the concentration zero-order $kd(s^{-1})$ | Depending on the concentration first-order $kd(s^{-1})$ | Diffusion controlled Higuchi $kd(s^{-1/2})$ |
|---|---|---|---|---|
| KYNA | 25° C. | $6.3 * 10^{-1}$ | $7.9 * 10^{-3}$ | **$6.9 * 10^{-0}$** |
| | 37.5° C. | $6.2 * 10^{-3}$ | $9.8 * 10^{-3}$ | **$7.0 * 10^{-0}$** |
| BSA/KYNA | 25° C. | $2.8 * 10^{-2}$ | $8.9 * 10^{-2}$ | **$1.1 * 10^{-1}$** |
| | 37.5° C. | $2.2 * 10^{-1}$ | $9.6 * 10^{-2}$ | **$1.5 * 10^{-0}$** |
| BSA/KYNA/PAH | 25° C. | **$4.2 * 10^{-2}$** | $8.6 * 10^{-4}$ | $5.2 * 10^{-1}$ |
| | 37.5° C. | **$1.7 * 10^{-1}$** | $1.9 * 10^{-3}$ | $1.6 * 10^{-0}$ |

The permeability of KYNA through the blood-brain barrier from BSA/KYNA/PAH nanocapsules was determined by means of an in vitro blood-brain barrier model. The description of the model is the following: microvessel rat brain endothelial cells were isolated from 2 to 3 weeks old Wistar animals by means of a method described earlier (Wilhelm és munkatársai, 2011). After the removal of the meninges, the brain tissue was dissectioned to small pieces, then it was digested by type 2 collagenase and collagenase/dispase, finally it was centrifuged on percoll gradient. The microvessel fragments were plated on collagenIV/fibronectin-coated Petri dishes and were cultured in DMEM/F12 in the presence of plasma serum and growth factors. To remove the impurity cells, the cultures were treated with puromycin on the first two days. Some of the microvessel fragments were plated onto non-coated Petri dishes, and were cultured in DMEM in the presence of foetal bovine serum, thus pericytes were obtained.

Figure 9:
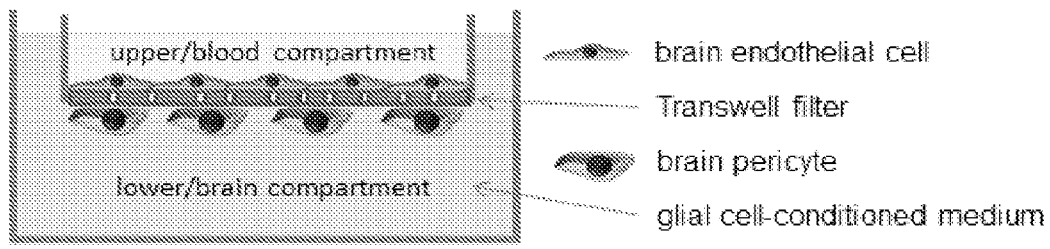
FIG. 9: A schematic figure of the in vitro blood-brain barrier model.

The investigation of the KYNA permeability was performed as follows (FIG. 9). Onto the backside of semipermeable filters (pore size: 0.4 µm, material: polyester), pericytes, onto the upper sides glial endothelial cells were plated. In order to improve the barrier characteristics of the confluent endothelic layer cAMP and hydrocortisone were placed into the upper compartment, and culturing liquid conditioned on glial cells was placed in the lower compartment for 24 hours. The monitoring of the transendothelial electric resistance was made possible with a CellZscope instrument (nanoAnalytics, Münster, Germany).

The cells were washed with Ringer-HEPES solution, and the free KYNA and the BSA/KYNA/PAH nanocapsules were added to the upper compartment in 20 µM KYNA final concentration. After one hour a sample was taken from the backside compartments.

From these samples the concentration of KYNA was determined using an Agilent 1100 HPLC-MS system (Agilent Technologies, Santa Clara, Calif., USA).

To calculate the permeability coefficient the following formulae were applied: $P_{app}dQ/(dT \times A \times C_0)$, wherein dQ stands for the crossed amount of the material, dT stands for the incubation period of time (1 hour), A stands for the surface of the filter and $C_0$ stands for the starting concentration (20 µM). The values thus calculated were compared to the values measured on empty (not containing cells) filters according to the following method: $P_e = P_{app} \times P_{app(filter)} - P_{app}$).

The value of $P_e$ is $3.71*10^{-6}$ cm/s ($\pm 3.64*10^{-7}$ cm/s) in case of the free KYNA, which is comparable with the permeability of Na-fluoresceine ($2.96*10^{-6}$ cm/s $\pm 8.78*10^{-7}$ cm/s)

Figure 10:
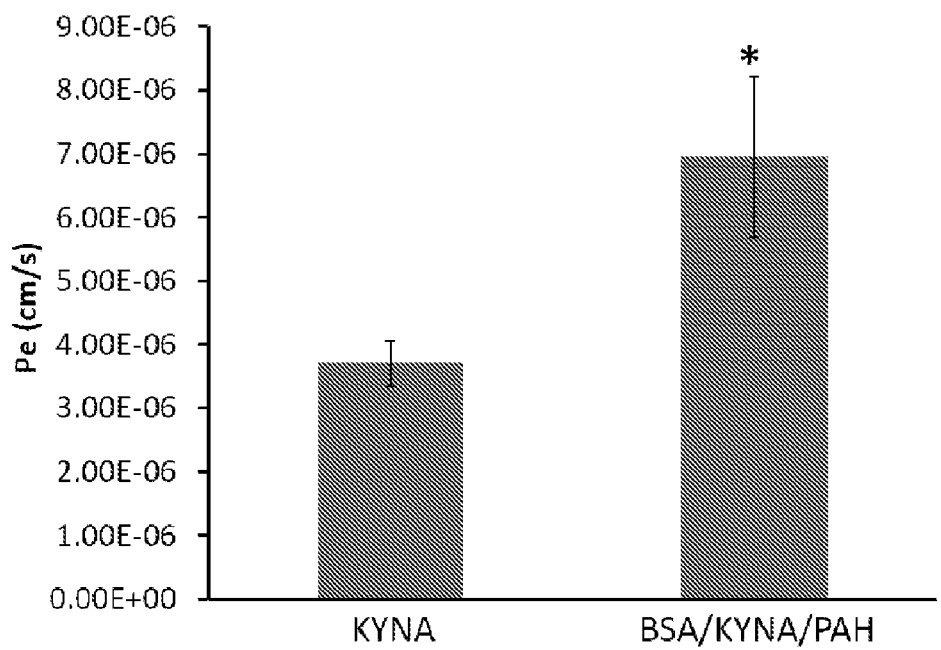
FIG. 10: Permeability of the KYNA and BSA/KYNA/PAH nanocomposite, respectively, with deviation through the brain endothelial cells *P<0.05 (n=3).

(FIG. 10). The permeability coefficient of KYNA from the BSA/KYNA/PAH nanocapsule was significantly higher (approx. 1.9 times): $6.95*10^{-6}$ cm/s ($\pm 1.26*10^{-6}$ cm/s).

Based on the results it can be established that significantly higher amount of KYNA crosses the blood-brain barrier from the BSA/KYNA/PAH nanocapsule, as compared to the free KYNA.

Figure 11:
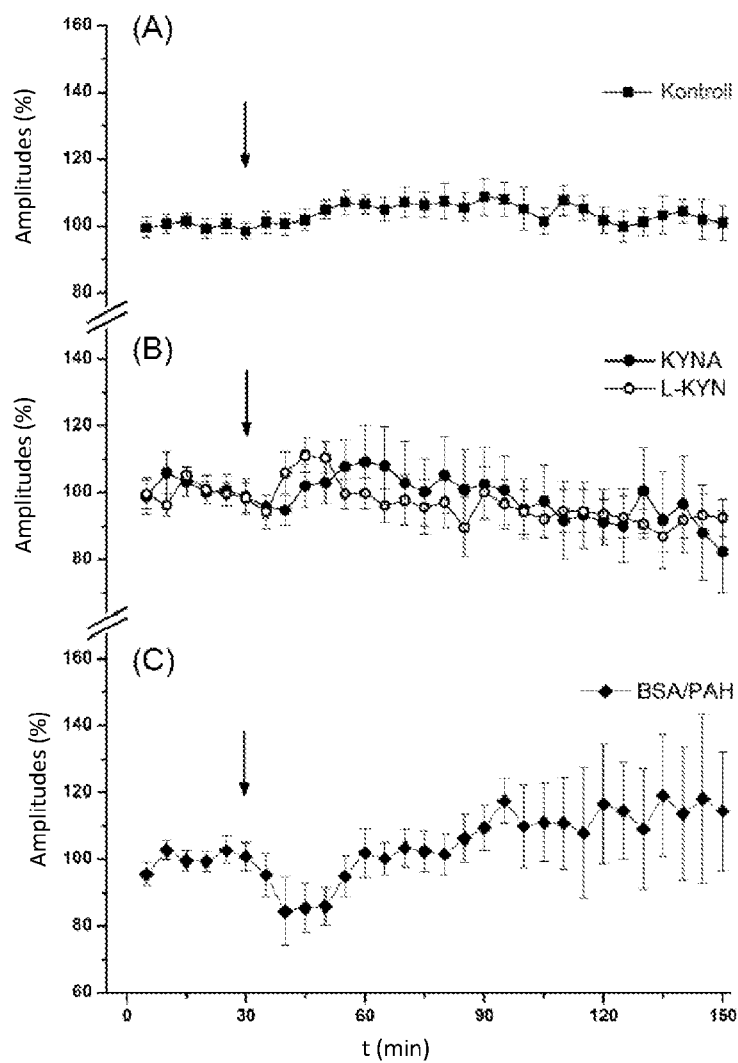
FIG. 11: Changes of amplitudes of somatosensory evoked potentials (SEPs) in the case of the (A) control group (n=5, injection of saline solution), (B) KYNA (300 mg/kg, n=5) as well as the administration of L-KYN (300 mg/kg, n=5), respectively, furthermore (C) for the empty BSA/PAH composite (n=6).

FIG. 11 shows the results of the in vivo experiments. There was no registered change in the measured amplitude in case of the control group during the test period. After intraperitoneal administration of KYNA and L-KYN, no significant change was experienced, either. After the administration of the empty BSA/PAH composite a short, slight and sudden amplitude decrease was experienced, then the amplitude was restored to the original level, but significant difference was not demonstrated here after the comparison with the control, either.

Figure 12:
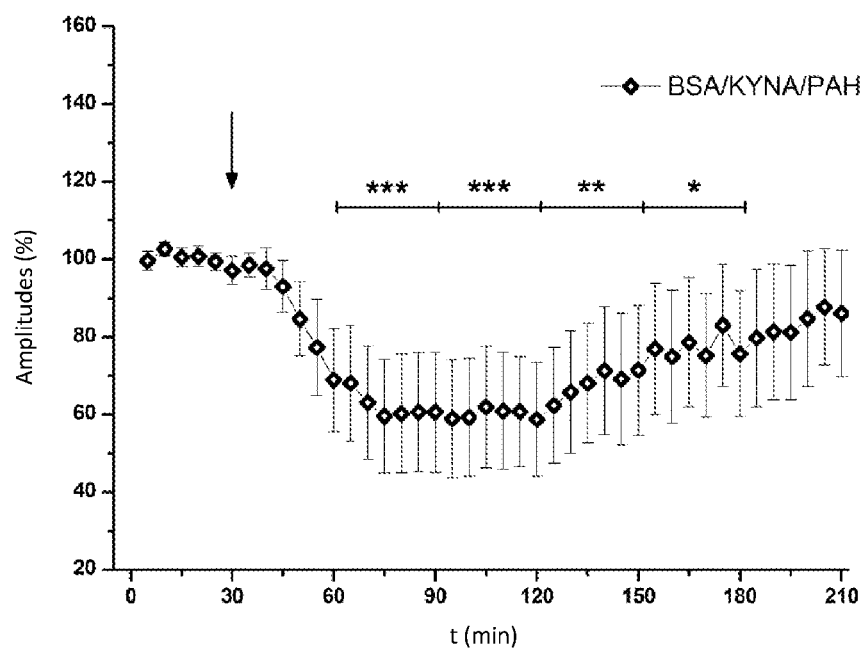
FIG. 12: Change in the measured amplitudes after the BSA/KYNA/PAH nanocomposite administration (n=9), wherein *P<0.05, P<0.01 and *P<0.001.

In case of the BSA/KYNA/PAH composite according to the present patent application (FIG. 12) the measured signal of the amplitude was decreased by 60% already 30 minutes after the administration, and the effect was maintained for a longer period of time (60 minutes). Following this a slow increase in the amplitude was experienced, then after 210 minutes it converged to the signal of the control sample.

Controlled Active Ingredient Release System

So far it has been demonstrated that the nanocomposite prepared was proven to be successful in carrying of KYNA. It was seen that both in the preparation and in the testing conditions the pH is 7.4 with constant ion strength (154 mM NaCl). However, the KYNA still gradually dissolves from the composite, see the in vitro (25 és 37.5° C.), and in vivo tests, where the KYNA crossing the blood-brain barrier exerts its effect in the central nervous system. Consequently, the binding of KYNA to BSA is reversible, thus as a result of the diffusion and chemical potential the BSA "releases" the active ingredient. The controlled (gradual, slow increase) dissolution demonstrates (also on the basis of the TEM images) that the polyelectrolyte encompasses the BSA/KYNA composite, thereby ensures the controlling of the release rate of the active ingredient.

The system according to the present invention is useful for the carrying, releasing of drug molecules through the blood-brain barrier into the central nervous system.

Hereinafter the most important characteristics of the present invention will be summarized.

The invention relates to a core-shell composites, which are suitable for the controlled release of active ingredients, especially pharmaceutically active ingredients into the central nervous system.

1. The protein constituting the core being present in native conformation (bovine serum albumin, human serum albumin, lysosyme, pH=7.4, c=4-30 w/v %), is prepared with a diameter of 5-10 nm, which ensures the encapsulation of the active ingredient molecule to the binding points of the protein, while ensures the dispersibility of the protein in an aqueous medium.

2. Other, biocompatible, biodegradable materials are also suitable to use in the form of the core constituting the composite, which, binding the drug molecules, as carrier systems may be used in the nanocapsules, for example hyaluronic acid, poly(lactic-co-glycolic acid).

3. The polyelectrolyte shell(s) (one or more depending on the stability of the composite), which can form a kind of interaction with the core including the active ingredient (hydrogen bond, electrostatic, hydrophobic, π-π interaction) are added to the core.

4. Neurotransmitters (dopamine, kynurenic acid), as well as non-steroidal anti inflammatory agents (acetylic salicylic acid, ibuprofen, ketoprofen, paracetamol, algopyrin) are used as active ingredient of the core-shell composite.

5. Other active ingredients may also be encapsulated in the core of the composite, which otherwise, due to their structural or other barrier factors are unable to cross the blood-brain barrier.

6. Other vitamins [alpha-tocopherol (vitamin E) and its derivatives)], furthermore, vitamins together with active ingredients may be packaged together in the capsules, and may be applied as active ingredients constituting the composite.

7. Depending on the stability of the active ingredient constituting the composite the medium of the synthesis may be selected (MQ, PBS, HEPES buffer, other buffer).

EXAMPLES

Example 1

Reversible interaction was formed between 0.9 mM concentration of BSA and 0.15 mM concentration of KYNA in an aqueous medium (3 ml). The molar ratio of the protein and the active ingredient was 1:175, their weight ratio was 1:0.5. The preparation of the composite took place in MQ water, by setting the pH to 7.4. The concentration of the polyelectrolite, PAH was 0.24 w/v % (0.16 mM). The shell was also dissolved in water, setting the pH to 7.4. The total volume was in all cases 3 ml physiological saline solution (150 mM NaCl).

Example 2

Reversible interaction was formed between 0.6-4.5 mM concentration of BSA solution and 0.12-1000 mM concentration of KYNA solution in an aqueous medium (1-5 ml). The molar ratio of the protein and the active ingredient was 1:0.2-222, their weight ratio was 1:0.00057-0.7. The preparation of the composite took place in MQ water, by setting the pH to 7.4. For the preparation of a one-layer core-shell composite the concentration of the polyelectrolite, PAH was in the range of 0.04-1.5 w/v %. The shell was also dissolved in MQ water, setting the pH to 7.4. The total volume was in all cases 1-5 ml physiological saline solution (150 mM NaCl).

Example 3

Reversible interaction was formed between 0.9 mM concentration of BSA and 0.15 mM concentration of sodium kynurenate in an aqueous medium (3 ml). The molar ratio of the protein and the (sodium salt derivative of the) active ingredient was 1:175, their weight ratio was 1:0.5. The preparation of the composite took place in MQ water, by setting the pH to 7.4. The concentration of the polyelectrolyte shell, PAH was 0.24 w/v % (0.16 mM). The shell was also dissolved in MQ water, setting the pH to 7.4. The total volume was in all cases 3 ml physiological saline solution (150 mM NaCl).

Example 4

Reversible interaction was formed between 0.6-1.5 mM concentration of BSA solution and 0.12-1000 mM concentration of sodium kynurenate solution in an aqueous medium (1-5 ml). The molar ratio of the protein and the (sodium salt derivative of the) active ingredient was 1:0.2-222, their weight ratio was 1:0.00057-0.7. The shell was also dissolved in MQ water, setting the pH to 7.4. For the preparation of a one-layer core-shell composite the concentration of the polyelectrolyte shell, PAH was in the range of 0.04-1.5 w/v %. The shell was also dissolved in MQ water, having a pH of 7.4. The total volume was in all cases 1-5 ml physiological saline solution (150 mM NaCl).

Example 5

Reversible interaction was formed between 0.9 mM concentration of BSA and 0.15 mM concentration of dopamine in an aqueous medium (3 ml). The molar ratio of the protein and the active ingredient was 1:175, their weight ratio was 1:0.5. The preparation of the composite took place in HEPES buffer, by setting the pH to 7.4. The concentration of the polyelectrolyte shell, PAH was 0.24 w/v % (0.16 mM). The shell was also dissolved in HEPES buffer, setting the pH to 7.4. The total volume was in all cases 3 ml physiological saline solution (150 mM NaCl).

Example 6

Reversible interaction was formed between 0.6-4.5 mM concentration of BSA solution and 0.12-1000 mM concentration of dopamine (DOPA) solution in an aqueous medium (1-5 ml). The molar ratio of the protein and the active ingredient was 1:0.2-222, their weight ratio was 1:0.00057-0.7. The preparation of the composite took place in HEPES buffer, at pH=7.4. For the preparation of a one-layer core-shell composite the concentration of the polyelectrolyte shell, PAH varied in the range of 0.04-1.5 w/v %. The shell was also dissolved in HEPES buffer, having a pH of 7.4. The total volume was in all cases 1-5 ml physiological saline solution (150 mM NaCl).

Example 7

Reversible interaction was formed between 0.9 mM concentration of BSA and 0.15 mM concentration of IBU in an aqueous medium (3 ml). The molar ratio of the protein and the (sodium salt derivative of the) active ingredient was 1:175, their weight ratio was 1:0.5. The preparation of the composite took place in phosphate buffer, by setting the pH to 7.4. The concentration of the polyelectrolyte shell, PAH was 0.24 w/v % (0.16 mM). The shell was also dissolved in PBS buffer, setting the pH to 7.4. The total volume was in all cases 3 ml physiological saline solution (150 mM NaCl).

Example 8

Reversible interaction was formed between 0.6-4.5 mM concentration of BSA and 0.12-1000 mM concentration of IBU solution in an aqueous medium (1 to 5 ml). The molar ratio of the protein and the (sodium salt derivative of the) active ingredient was 1:0.2-222, their weight ratio was 1:0.00057-0.7. The preparation of the composite took place in phosphate buffer, by setting the pH to 7.4. For the preparation of the one-layer core-shell composite the concentration of the polyelectrolyte shell, PAH varied in the range of 0.04 to 1.5 w/v %. The shell was also dissolved in PBS buffer, setting the pH to 7.4. The total volume was in all cases 1-5 ml physiological saline solution (150 mM NaCl).

Example 9

The release tests were made in case of KYNA in PBS buffer at pH=7.4. (physiological solution). Due to the stability of KYNA at this pH in physiological environment it demonstrated stability until 72 hours, thus the stability tests took place within this period of time.

Example 10

The release tests were made in case of DOPA in HEPES buffer at pH=7.4. (physiological solution). Due to the stability of DOPA at this pH in physiological environment it demonstrated stability until 72 hours, thus the stability tests took place within this period of time.

Example 11

The release tests were made in case of IBU in PBS buffer at pH=7.4. (physiological solution). Due to the stability of KYNA at this pH in physiological environment it demonstrated stability until 96 hours, thus the stability tests took place within this period of time.

Example 12

Core-shell composites were also made in the presence of vitamin E, as well. Reversible interaction was formed between 0.9 mM concentration of BSA, 0.15 mM concentration of KYNA, furthermore 0.2 mM concentration of vitamin E (mixed with ethanol, then the alcohol was evaporated) in an aqueous medium (3 ml). The molar ratio of the protein and the KYNA was 1:175, their weight ratio was 1:0.5. The weight ration of KYNA and vitamin E was 1:1. The preparation of the composite took place in MQ water, by setting the pH to 7.4. The concentration of the polyelectrolyte shell, PAH was 0.24 w/v % (0.16 mM). The shell was also dissolved in MQ water, setting the pH to 7.4. The total volume was in all cases 3 ml physiological saline solution (150 mM NaCl).

Example 13

Reversible interaction was formed between 0.6-4.5 mM concentration of BSA, 0.12-1000 mM concentration of KYNA, furthermore 0.00878-440 mM concentration of vitamin E (mixed with ethanol, then the alcohol was evaporated) in an aqueous medium (1-5 ml). The molar ratio of the protein and the KYNA was 1:0.2-222, their weight ratio was 1:0.00057-0.7. The weight ration of KYNA and vitamin E was 1:0.1-10. The preparation of the composite took place in MQ water, by setting the pH to 7.4. For the preparation of the one-layer core-shell composite the concentration of the polyelectrolyte shell, PAH varied in the range of 0.04-1.5 w/v %. The shell was also dissolved in MQ water, setting the pH to 7.4. The total volume was in all cases 1-5 ml physiological saline solution (150 mM NaCl).

Example 14

Core-shell composites were also made in the presence of vitamin E, as well. Reversible interaction was formed between 0.9 mM concentration of BSA, 0.15 mM concentration of KYNA, furthermore 0.2 mM concentration of vitamin E (mixed with acetone, then the ketone was evaporated) in an aqueous medium (3 ml). The molar ratio of the protein and the KYNA was 1:175, their weight ratio was 1:0.5. The weight ration of KYNA and vitamin E was 1:1. The preparation of the composite took place in MQ water, by setting the pH to 7.4. The concentration of the polyelectrolyte shell, PAH was 0.24 w/v % (0.16 mM). The shell was also dissolved in MQ water, setting the pH to 7.4. The total volume was in all cases 3 ml physiological saline solution (150 mM NaCl).

Example 15

Reversible interaction was formed between 0.6-4.5 mM concentration of BSA, 0.12-1000 mM concentration of KYNA, furthermore 0.00878-440 mM concentration of vitamin E (mixed with acetone, then the ketone was evaporated) in an aqueous medium (1-5 ml). The molar ratio of the protein and the KYNA was 1:0.2-222, their weight ratio was 1:0.00057-0.7. The weight ration of KYNA and vitamin E was 1:0.1-10. The preparation of the composite took place in MQ water, by setting the pH to 7.4. For the preparation of the one-layer core-shell composite the concentration of the polyelectrolyte shell, PAH varied in the range of 0.04-1.5 w/v %. The shell was also dissolved in MQ water, setting the pH to 7.4. The total volume was in all cases 1-5 ml physiological saline solution (150 mM NaCl).

Example 16

Core-shell composites were also made in the presence of vitamin E, as well. Reversible interaction was formed between 0.9 mM concentration of BSA, 0.15 mM concentration of sodium kynurenate, furthermore 0.2 mM concentration of vitamin E (mixed with ethanol, then the alcohol was evaporated) in an aqueous medium (3 ml). The molar ratio of the protein and the sodium kynurenate was 1:175, their weight ratio was 1:0.5. The weight ration of sodium kynurenate and vitamin E was 1:1. The preparation of the composite took place in MQ water, by setting the pH to 7.4. The concentration of the polyelectrolyte shell, PAH was 0.24 w/v % (0.16 mM). The shell was also dissolved in MQ water, setting the pH to 7.4. The total volume was in all cases 3 ml physiological saline solution (150 mM NaCl).

Example 17

Reversible interaction was formed between 0.6-4.5 mM concentration of BSA, 0.12-1000 mM concentration of sodium kynurenate, furthermore 0.00878-440 mM concentration of vitamin E (mixed with ethanol, then the alcohol was evaporated) in an aqueous medium (1-5 ml). The molar ratio of the protein and the sodium kynurenate was 1:0.2-222, their weight ratio was 1:0.00057-0.7. The weight ration of sodium kynurenate and vitamin E was 1:0.1-10. The preparation of the composite took place in MQ water, by setting the pH to 7.4. For the preparation of the one-layer core-shell composite the concentration of the polyelectrolyte shell, PAH varied in the range of 0.04-1.5 w/v %. The shell was also dissolved in MQ water, setting the pH to 7.4. The total volume was in all cases 1-5 ml physiological saline solution (150 mM NaCl).

Example 18

Core-shell composites were also made in the presence of vitamin E, as well. Reversible interaction was formed between 0.9 mM concentration of BSA, 0.15 mM concentration of sodium kynurenate, furthermore 0.2 mM concentration of vitamin E (mixed with acetone, then the ketone was evaporated) in an aqueous medium (3 ml). The molar ratio of the protein and the sodium kynurenate was 1:175, their weight ratio was 1:0.5. The weight ration of sodium kynurenate and vitamin E was 1:1. The preparation of the composite took place in MQ water, by setting the pH to 7.4. The concentration of the polyelectrolyte shell, PAH was 0.24 w/v % (0.16 mM). The shell was also dissolved in MQ water, setting the pH to 7.4. The total volume was in all cases 3 ml physiological saline solution (150 mM NaCl).

Example 19

Reversible interaction was formed between 0.6-4.5 mM concentration of BSA, 0.12-1000 mM concentration of sodium kynurenate, furthermore 0.00878-440 mM concentration of vitamin E (mixed with acetone, then the ketone was evaporated) in an aqueous medium (1-5 ml). The molar ratio of the protein and the sodium kynurenate was 1:0.2-222, their weight ratio was 1:0.00057-0.7. The weight ration of sodium kynurenate and vitamin E was 1:0.1-10. The preparation of the composite took place in MQ water, by setting the pH to 7.4. For the preparation of the one-layer core-shell composite the concentration of the polyelectrolyte shell, PAH varied in the range of 0.04-1.5 w/v %. The shell was also dissolved in MQ water, setting the pH to 7.4. The total volume was in all cases 1-5 ml physiological saline solution (150 mM NaCl).

Example 20

Core-shell composites were also made in the presence of vitamin E, as well. Reversible interaction was formed between 0.9 mM concentration of BSA, 0.15 mM concentration of DOPA, furthermore 0.2 mM concentration of vitamin E (mixed with ethanol, then the alcohol was evaporated) in an aqueous medium (3 ml). The molar ratio of the protein and the DOPA was 1:175, their weight ratio was 1:0.5. The weight ration of DOPA and vitamin E was 1:1. The preparation of the composite took place in HEPES buffer, by setting the pH to 7.4. The concentration of the polyelectrolyte shell, PAH was 0.24 w/v % (0.16 mM). The shell was also dissolved in HEPES buffer, setting the pH to 7.4. The total volume was in all cases 3 ml physiological saline solution (150 mM NaCl).

Example 21

Reversible interaction was formed between 0.6-4.5 mM concentration of BSA, 0.12-1000 mM concentration of DOPA, furthermore 0.00878-440 mM concentration of vitamin E (mixed with ethanol, then the alcohol was evaporated) in an aqueous medium (1-5 ml). The molar ratio of the protein and the DOPA was 1:0.2-222, their weight ratio was 1:0.00057-0.7. The weight ration of DOPA and vitamin E was 1:0.1-10. The preparation of the composite took place in MQ water, by setting the pH to 7.4. For the preparation of the one-layer core-shell composite the concentration of the polyelectrolyte shell, PAH varied in the range of 0.04-1.5 w/v %. The shell was also dissolved in HEPES buffer, setting the pH to 7.4. The total volume was in all cases 1-5 ml physiological saline solution (150 mM NaCl).

Example 22

Core-shell composites were also made in the presence of vitamin E, as well. Reversible interaction was formed between 0.9 mM concentration of BSA, 0.15 mM concentration of DOPA, furthermore 0.2 mM concentration of vitamin E (mixed with acetone, then the ketone was evaporated) in an aqueous medium (3 ml). The molar ratio of the protein and the DOPA was 1:175, their weight ratio was 1:0.5. The weight ration of DOPA and vitamin E was 1:1. The preparation of the composite took place in HEPES buffer, by setting the pH to 7.4. The concentration of the polyelectrolyte shell, PAH was 0.24 w/v % (0.16 mM).

The shell was also dissolved in HEPES buffer, setting the pH to 7.4. The total volume was in all cases 3 ml physiological saline solution (150 mM NaCl).

Example 23

Reversible interaction was formed between 0.6-4.5 mM concentration of BSA, 0.12-1000 mM concentration of DOPA, furthermore 0.00878-440 mM concentration of vitamin E (mixed with acetone, then the ketone was evaporated) in an aqueous medium (1-5 ml). The molar ratio of the protein and the DOPA was 1:0.2-222, their weight ratio was 1:0.00057-0.7. The weight ration of DOPA and vitamin E was 1:0.1-10. The preparation of the composite took place in MQ water, by setting the pH to 7.4. For the preparation of the one-layer core-shell composite the concentration of the polyelectrolyte shell, PAH varied in the range of 0.04-1.5 w/v %. The shell was also dissolved in HEPES buffer, setting the pH to 7.4. The total volume was in all cases 1-5 ml physiological saline solution (150 mM NaCl).

Example 24

Core-shell composites were also made in the presence of vitamin E, as well. Reversible interaction was formed between 0.9 mM concentration of BSA, 0.15 mM concentration of IBU, furthermore 0.2 mM concentration of vitamin E (mixed with ethanol, then the alcohol was evaporated) in an aqueous medium (3 ml). The molar ratio of the protein and the IBU was 1:175, their weight ratio was 1:0.5. The weight ration of IBU and vitamin E was 1:1. The preparation of the composite took place in PBS buffer, by setting the pH to 7.4. The concentration of the polyelectrolyte shell, PAH was 0.24 w/v % (0.16 mM). The shell was also dissolved in PBS buffer, setting the pH to 7.4. The total volume was in all cases 3 ml physiological saline solution (150 mM NaCl).

Example 25

Reversible interaction was formed between 0.6-4.5 mM concentration of BSA, 0.12-1000 mM concentration of IBU, furthermore 0.00878-440 mM concentration of vitamin E (mixed with ethanol, then the alcohol was evaporated) in an aqueous medium (1-5 ml). The molar ratio of the protein and the IBU was 1:0.2-222, their weight ratio was 1:0.00057-0.7. The weight ration of IBU and vitamin E was 1:0.1-10. The preparation of the composite took place in PBS buffer, by setting the pH to 7.4. For the preparation of the one-layer core-shell composite the concentration of the polyelectrolyte shell, PAH varied in the range of 0.04-1.5 w/v %. The shell was also dissolved in PBS buffer, setting the pH to 7.4. The total volume was in all cases 1-5 ml physiological saline solution (150 mM NaCl).

Example 26

Core-shell composites were also made in the presence of vitamin E, as well. Reversible interaction was formed between 0.9 mM concentration of BSA, 0.15 mM concentration of IBU, furthermore 0.2 mM concentration of vitamin E (mixed with acetone, then the ketone was evaporated) in an aqueous medium (3 ml). The molar ratio of the protein and the IBU was 1:175, their weight ratio was 1:0.5. The weight ration of IBU and vitamin E was 1:1. The preparation of the composite took place in PBS buffer, by setting the pH to 7.4. The concentration of the polyelectrolyte shell, PAH was 0.24 w/v % (0.16 mM). The shell was also dissolved in PBS buffer, setting the pH to 7.4. The total volume was in all cases 3 ml physiological saline solution (150 mM NaCl).

Example 27

Reversible interaction was formed between 0.6-4.5 mM concentration of BSA, 0.12-1000 mM concentration of IBU, furthermore 0.00878-440 mM concentration of vitamin E (mixed with acetone, then the ketone was evaporated) in an aqueous medium (1-5 ml). The molar ratio of the protein and the IBU was 1:0.2-222, their weight ratio was 1:0.00057-0.7. The weight ration of IBU and vitamin E was 1:0.1-10. The preparation of the composite took place in PBS buffer, by setting the pH to 7.4. For the preparation of the one-layer core-shell composite the concentration of the polyelectrolyte shell, PAH varied in the range of 0.04-1.5 w/v %. The shell was also dissolved in PBS buffer, setting the pH to 7.4. The total volume was in all cases 1-5 ml physiological saline solution (150 mM NaCl).

INDUSTRIAL APPLICABILITY

The nanocomposite according to the present invention is useful for the controlled release of an active ingredient into the central nervous system. The process according to the invention is useful for the preparation of the nanocomposite within upscaled pharmaceutical industrial conditions.

What is claimed is:

1. Nanocomposite of an active ingredient for the controlled release into the central nervous system, and/or for decreasing the peripheric side effects of the active ingredients, said nanocomposite consisting of
   a) a core-part, which comprises a biocompatible, biodegrading material, which can reversibly bind the active ingredients and release them at a target area, wherein the concentration of the biocompatible, biodegrading material in the core is 4-30 w/v %, and the diameter of the core is 5-10 nm,
   b) a one-layer shell-part, which consists of a polyelectrolyte, which can form a chemical bond with the material of the core-part, and optionally one or more other biocompatible material, wherein the concentration of the polyelectrolyte in the shell-part is 0.04-1.5 w/v %, characterized in that the core-part and the shell-part are linked to each other by a chemical bond, c) one or more active ingredient selected from the group consisting of kynurenic acid (KYNA), sodium kynurenate, dopamine (DOPA) and ibuprofen (IBU), and d) optionally an adjuvant which facilitates the crossing of the active ingredient through the blood-brain barrier wherein the biocompatible, biodegrading material is bovine serum albumin (BSA), wherein the polyelectrolyte is poly(allylamine hydrochloride) (PAH), wherein the active ingredient is reversibly bound to the core-part by one or more reversible bond(s) selected from the group consisting of hydrogen-bridge, hydrophobic and π-π interactions, and wherein the bovine serum albumin in the nanocomposite has an α-helix content lower than in its native form.

2. The nanocomposite as claimed in claim 1, wherein the hydrodynamic diameter of the nanocomposite without active ingredient is d=20.5 nm (SD=±1.2 nm), measured with a HORIBA SZ-100 type dynamic light scattering measuring device, zeta potential is $\zeta$=−2.8 mV (SD=±0.2 mV), and the diameter of the core determined by SAX measuring, using a Philips, PW-1830 equipment is D=12.5 nm (SD=±0.3 nm).

3. The nanocomposite as claimed in claim 1, characterized in that it possesses the following sizes and structural characteristics:

a) when the active ingredient is kynurenic acid: the hydrodynamic diameter of the nanocomposite is d=103.4 nm (SD=±4.8 nm), measured with a HORIBA SZ-100 type dynamic light scattering measuring device, the zeta potential is $\zeta$=−6.5 mV (SD=±0.3 mV), and the diameter of the core determined by SAXS measuring, using a Philips, PW-1830 equipment is D=10.2 rim (SD=±0.3 nm);

b) when the active ingredient is dopamine: the hydrodynamic diameter of the nanocomposite is d=101.9 nm (SD=±5.3 nm), measured with a HORIBA SZ-100 type dynamic light scattering measuring device, the zeta potential is $\zeta$=−7.1 mV (SD=±0.3 mV), and the diameter of the core determined by SAXS measuring, using a Philips, PW-1830 equipment is D=11.1 nm (SD=±0.4 nm);

c) when the active ingredient is ibuprofen: the hydrodynamic diameter of the nanocomposite is d=99.8 nm (SD=±2.5 nm), measured with a HORIBA SZ-100 type dynamic light scattering measuring device, the zeta potential is $\zeta$=−6.8 mV (SD=±0.4 mV), and the diameter of the core determined by SAXS measuring, using a Philips, PW-1830 equipment is D=10.5 nm (SD=±0.1 nm).

4. Process for the preparation of the nanocomposite as claimed in claim 1, characterized in that the following steps are performed:

a) the biocompatible, biodegrading material constituting the core-part is prepared in native conformation, with a diameter of 5-10 nm;

b) a reversible interaction is formed between the core-biocompatible, biodegrading material and the active ingredient in an aqueous media or in an a buffer;

c) the polyelectrolyte constituting the shell-part is added to the core as prepared in step b), comprising the biocompatible, biodegrading material and active ingredient;

wherein the preparation of the nanocomposite takes place within physiological environment at a pH between 6.5 and 7.5.

5. The nanocomposite as claimed in claim 1 for the controlled release of active ingredients into the central nervous system, and/or for decreasing the peripheric side effects of the active ingredients.

6. A pharmaceutical composition comprising the nanocomposite as claimed in claim 1.

7. A method for the controlled release of an active ingredient into the central nervous system, and/or for decreasing the peripheric side effects of the active ingredient, said method comprising administering the nanocomposite of claim 1 to a subject.

8. The method of claim 7, wherein the active ingredient is carried though the blood-brain barrier.

9. The nanocomposite as claimed in claim 7, comprising the adjuvant which facilitates the crossing of the active ingredient through the blood-brain barrier.

10. The nanocomposite as claimed in claim 9, wherein the adjuvant is vitamin E.

11. The nanocomposite as claimed in claim 1, wherein the active ingredient is selected form the group consisting of kynurenic acid, sodium kynurenate and dopamine.

12. The nanocomposite as claimed in claim 1, wherein the active ingredient is ibuprofen.

* * * * *